United States Patent [19]

Lee-Huang et al.

[11] Patent Number: 5,532,214

[45] Date of Patent: Jul. 2, 1996

[54] ANTI-HIV PROTEIN, TAP 29, FROM TRICOSANTHES, DNA CODING THEREFOR AND THERAPEUTIC USES THEREOF

[75] Inventors: Sylvia Lee-Huang, New York, N.Y.; Philip L. Huang, Boston, Mass.; Hao-chia Chen, Potomac; Hsiang-fu Kung, Middletown, both of Md.; Peter Huang; Henry I. Huang, both of New York, N.Y.; Paul L. Huang, Boston, Md.

[73] Assignees: New York University, New York, N.Y.; American Biosciences, Inc., Boston, Mass.; The United States of America as represented by the Department of Health and Human Services, Washington, D.C.

[21] Appl. No.: 275,327

[22] Filed: Jul. 14, 1994

Related U.S. Application Data

[63] Continuation of Ser. No. 966,600, Oct. 26, 1992, abandoned, which is a continuation of Ser. No. 685,126, Apr. 15, 1991.

[51] Int. Cl.$^6$ ................................................. A61K 38/02
[52] U.S. Cl. ................................................. 214/2; 530/370
[58] Field of Search ............................ 530/370; 514/2, 514/8; 435/974

[56] References Cited

U.S. PATENT DOCUMENTS

| | | | |
|---|---|---|---|
| 4,795,739 | 1/1989 | Lifson et al. | 530/370 |
| 4,985,541 | 1/1991 | Maraganore et al. | 530/397 |
| 5,037,960 | 8/1991 | Barbieri et al. | 530/370 |
| 5,077,390 | 12/1991 | Wu et al. | 530/370 |
| 5,149,528 | 9/1992 | Maraganore et al. | 424/85.91 |
| 5,166,056 | 11/1992 | Piatak et al. | 435/69.1 |

OTHER PUBLICATIONS

Johnston et al, Science 260 :1286–1293, 1993.
Ke et al, Immunophormacol. Immunotivial. 10(2):131–140, 1988.
Zarling et al., *Nature*, 347: 92–95 (1990).
McGrath et al, "GLQ223: A Inhibitor of Human Innunodeficiency virus. . . ", PNAS USA vol. 86, Apr. 1989. pp. 2844–2848.
Toyokawa, S., et al, *The Complete Amino Acid Sequence of an Abortifacient Protein, Karasurin*, Chem. Pharm. Bull., vol. 29, No. 5, pp. 1244–1249, 1991.
Lee–Huang, S., et al, *TAP 29: An Anti–human Immunodeficiency Virus Protein From Trichosanthes kirilowii that is Nontoxic to Intact Cells*, Proc. Natl. Acad. Sci. USA, vol. 88, pp. 6570–6574, Aug. 1991.

*Primary Examiner*—Michael P. Woodward
*Assistant Examiner*—Jeffrey Stucker
*Attorney, Agent, or Firm*—Browdy and Neimark

[57] ABSTRACT

A new protein, termed TAP 29, obtainable from the root tuber of the plant *Trichosanthes kirilowii* or produced by recombinant means is useful for treating HIV infections or tumors. In treating HIV infections, the protein is administered alone or in conjunction with conventional AIDS therapies. Also provided are processes for purifying the protein, DNA sequences encoding the protein, hosts expressing the protein, recombinant DNA methods for expressing the protein, and antibodies specific for the protein.

1 Claim, 4 Drawing Sheets

ANTI-HIV PROTEIN, TAP 29, FROM TRICOSANTHES, DNA CODING THEREFOR AND THERAPEUTIC USES THEREOF

This application is a continuation of application Ser. No. 07/966,600filed Oct. 26, 1992, now abandoned, which is a continuation of application Ser. No. 07/685,126, filed Apr. 15, 1991.

FIELD OF THE INVENTION

The present invention in the fields of virology and oncology relates to TAP 29, a protein purified from Trichosanthes plant extracts and to uses therefor in treating HIV infection.

BACKGROUND OF THE INVENTION

HIV Infection and AIDS

Human Immunodeficiency Virus (HIV), the etiological agent for AIDS (Acquired Immune Deficiency Syndrome), is a member of the lentiviruses, a subfamily of retroviruses. Many retroviruses are well-known carcinogens. HIV per se is not known to cause cancer in humans or other animals, but it does present a formidable challenge to the host. HIV integrates its genetic information into the genome of the host. The viral genome contains many regulatory elements which allow the virus to control its rate of replication in both resting and dividing cells. Most importantly, HIV infects and invades cells of the immune system; it destroys the body's immune system and renders the patient susceptible to opportunistic infections and neoplasms. The immune defect appears to be progressive and irreversible, with a high mortality rate that approaches 100% over several years.

HIV is transmitted by parenteral inoculation and/or intimate sexual contact. It is estimated that about 2 million people in the United States are currently infected with HIV, and 5 to 10 million people are infected worldwide. Recent projections indicate that a majority of those now infected will develop AIDS within a seven year follow-up period. In 1989 alone, over 130,000 cases of AIDS were reported domestically, and more than half of these patients have died. It is estimated that an additional 200,000 cases will be diagnosed in the United States by the end of 1990. Reports to the World Health Organization suggest that at least a million new cases of AIDS can be expected within the next five years worldwide. It is apparent that AIDS is an unprecedented threat to U.S. as well as global health. The search for effective therapies to treat AIDS is of paramount importance.

HIV-1 is trophic and cytopathic for T4 lymphocytes, cells of the immune system which express the cell surface differentiation antigen CD4 (also known as OKT4, T4 and leu3). The viral tropism is due to the interactions between the viral envelope glycoprotein, gp120, and the cell-surface CD4 molecules (Dalgleish, A. G. et al., *Nature* 312: 763–767 (1984). These interactions not only mediate the infection of susceptible cells by HIV but are also responsible for the virus-induced fusion of infected and uninfected T cells. This cell fusion results in the formation of giant multinucleated syncytia, cell death, and progressive depletion of CD4 cells in AIDS patients. These events result in HIV-induced immunosuppression and its subsequent sequelae, opportunistic infections and neoplasms.

In addition to CD4+ T cells, the host range of HIV includes cells of the mononuclear phagocytic lineage (Dalgleish, A. G. et al., supra), including blood monocytes, tissue macrophages, Langerhans cells of the skin and dendritic reticulum cells within lymph nodes. HIV is also neurotropic, capable of infecting monocytes and macrophages in the central nervous system causing severe neurologic damage. Macrophage/monocytes are a major reservoir of HIV. They may interact and fuse with CD4-bearing T cells, causing T cell depletion and thus contributing to the pathogenesis of AIDS.

Anti-HIV Drugs

Intensive efforts are currently under way to develop therapies to prevent or intervene in the development of clinical symptoms in HIV-infected individuals. For the most part, efforts have been focused on the use of nucleoside analogue drugs such as AZT (azidothymidine), and on other dideoxynucleoside derivatives such as ddA, ddT, ddI, and ddC. These drugs inhibit the viral enzyme, reverse transcriptase, thereby inhibiting de novo infection of cells. However, once viral infection has been established within a cell, viral replication utilizes host cell enzymes. Thus, drugs which inhibit only reverse transcriptase would be expected to have limited effects. While the spread of free virus within the organism may be blocked, the mechanisms of syncytium formation and pathogenesis through direct intercellular spread remain.

A very small number of HIV-infected T cells can fuse with, and eventually kill, large numbers of uninfected T cells through mechanisms based on viral surface antigen expression. In vitro studies have demonstrated HIV replication even in the continued presence of nucleoside analogues in prolonged culture. Drugs targeting other viral processes are also being developed, such as soluble CD4 and dextran sulfate to inhibit viral binding, alpha interferons and "ampligen" to inhibit viral budding, and castanospermine to inhibit the processing of the viral glycoproteins. These drugs are still in early stages of testing. The actual processes of HIV intracellular replication and protein synthesis have not been specifically targeted because these viral functions were thought to reflect the mere pirating of normal host processes through host mechanisms.

Immunotoxins and Their Limitations

Immunotoxins, have been developed by conjugating a protein toxin to a monoclonal antibody via a linker for targeted therapy, in particular, of tumors (Vitetta, E. S. et al., *Ann. Rev. Immunol.* 3:197–212 (1985)). In principle, an injected immunotoxin is transported through the blood stream to the targeted tissue, penetrates the tissue, binds to the individual cells expressing the antigen to which the antibody is directed. The toxin bound to the antibody then acts in a highly localized manner to destroy only the cells to which the antibody is bound. All three components of the conjugates are important for the specific achievement of cytotoxicity: the antibody enables the conjugate to be retained in the target tissue by binding to a specific cell-surface antigen, which enhances cellular uptake by the target cells. The linker keeps the toxin bound to the antibody and inactive while in circulation, but allows for rapid release of the active toxin inside the target cells. The toxin kills the cell by inhibiting cellular protein synthesis, or by some other related mechanism.

Some of the most cytotoxic substances known are protein toxins of bacterial and plant origin (Frankel, A. E. et al., *Ann. Rev. Med.* 37:125–142 (1986)). The cytotoxic action of these molecules involves two events—binding the cell surface and inhibition of cellular protein synthesis. The most commonly used plant toxins are ricin and abrin; the most commonly used bacterial toxins are diphtheria toxin and Pseudomonas exotoxin A.

In ricin and abrin, the binding and toxic functions are contained in two separate protein subunits, the A and B chains. The ricin B chain binds to the cell surface carbohydrates and promotes the uptake of the A chain into the cell. Once inside the cell, the ricin A chain inhibits protein synthesis by inactivating the 60S subunit of the eukaryotic ribosome Endo, Y. et al., *J. Biol. Chem.* 262: 5908–5912 (1987)).

Diphtheria toxin and Pseudomonas exotoxin A are single chain proteins, and their binding and toxicity functions reside in different domains of the same protein chain. In diphtheria toxin, the C-terminal domain inhibits protein synthesis by ADP-ribosylation of the elongation factor, EF2. The two activities are separate, and the toxin elicits its full activity only after proteolytic cleavage between the two domains. Pseudomonas exotoxin A has the same catalytic activity as diphtheria toxin.

The use of diphtheria toxin-based immunotoxins is limited by the fact that most people have been immunized against diphtheria toxin. The use of ricin-based immunotoxins is also limited because these immunotoxins exhibit specific toxicity only in the presence of lactose, which at high concentrations competes with the cell surface carbohydrates for the B chain binding sites. An alternative approach has been developed to use ricin A chain or "single chain ribosome inactivating protein" (SCRIP) in the preparation of immunotoxins.

Single Chain Ribosome Inactivating Proteins (SCRIPs) and Their Potential Application in Antiviral or Tumor Therapy Trichosanthin, as well as the novel protein of the present invention, belong to the family of single chain ribosomeinactivating proteins (SCRIPs). SCRIPs are highly active at inactivating ribosomes in cell-free systems, but are relatively nontoxic to intact cells.

SCRIPs, also known as type 1 ribosome-inactivating proteins, catalytically inhibit in vitro eukaryotic protein synthesis (Stripe, F. et al., *FEBS Lett.* 195:1–8 (1986)). They specifically cleave the N-glycosidic linkage of adenosine at residue A4324 of eukaryotic 28S RNA (Endo, Y. et al., *J. Biol. Chem.* 262:8128–8130 (1987)). This impairs the interaction of the elongation factor EF2 with the 60S ribosomal subunit, thus abrogating polypeptide chain elongation. SCRIPs are basic proteins with a pI in the range of pH 8 to 10, and molecular weights in generally in the range of about 24 to 33 kDa.

A wide variety of SCRIPs are found in plants. In addition to trichosanthin, other plant-derived SCRIPs include *Momordica*-derived inhibitors (Barbieri, L. et al., *Biochem. J.* 186:443–452 (1980); Jimenez, A. et al., *Annu. Rev. Microbiol.* 39:649–672 (1985)), MAP 30, a protein recently isolated by some of the present inventors from *Momordica charantia*, which has potent anti-HIV activity with little cytotoxicity (Lee-Huang, S. et al., *FEBS Lett.* 272:12–18 (1990)), dianthins (Stripe, F. et al., *Biochem. J.* 195:399–405 (1981)), gelonin (Stripe, F. et al., *J. Biol. Chem.* 255:6947–53 (1980)), and the pokeweed anti-viral proteins (PAP) (Irvin, J. D., *Arch. Biochem. Biophys.* 169:522–528 (1975); Irvin, J. D. et al., *Arch. Biochem. Biophys.*200:418–425 (1980); Barbieri, L. et al., *Biochem. J.* 203:55–59 (1982)). Many of these SCRIPs are antiviral agents, and some also exhibit selective antitumor activity. SCRIPS and their conjugates, including trichosanthin (McGrath, M. S. et al., *Proc. Natl. Acad. Sci. USA* 86:2844–2848 (1989)) and PAP-anti-CD4 conjugate (Zarling, J. M. et al., *Nature* 347:92–95 (1990)) have been reported to possess anti-HIV activity, but have variable degrees of nonspecific cytotoxicity.

Recently, the primary amino acid sequence of α-trichosanthin and molecular models for abrin A-chain and α-trichosanthin were reported (Collins, E. J. et al., *J. Biol. Chem.* 265:8665–8669 (1990)). This α-trichosanthin sequence differs substantially from sequences reported by others for trichosanthin (Zhang, X. et al., *Nature* 321:477–478 (1986); Maraganore, J. Met al., *J. Biol. Chem.* 262:11628–11633 (1987)). This proposed structural model of trichosanthin differs from a previous model generated from x-ray diffraction data (Pan, K. St al., *Sci. Sin. Ser B.* (Chem. Biol. Agric. Med. & Earth Sci.) 30:386–395 (1987)). All of these trichosanthins were isolated from root tubers of the same species of *T. kirilowii*. However, no systematic comparison of the cytotoxicity and bioactivities of these proteins have been reported. In view of the therapeutic potential of these proteins, studies on the relationship between their structure and function may lead to the rational design and targeted development of safer and more effective second generation anti-HIV drugs.

M. S. McGrath et al. (supra) reported that GLQ 223, a SCRIP isolated from *T. kirilowii*, selectively inhibits HIV replication. This compound demonstrated dose-dependent anti-HIV activity in both acutely and chronically infected T cells and monocytes/macrophages. This discovery led to the rapid clinical testing of GLQ 223 as an anti-AIDS therapeutic. Treatment of cells with GLQ 223 resulted in selective inhibition of the synthesis of viral DNA, RNA, and protein, with less effect on cellular synthesis. Inhibition of viral replication occurred at GLQ 223 concentrations that had less of an effect on uninfected cells.

The mechanisms of the selective anti-HIV activity of GLQ 223 is not known. It has not been established whether this activity is associated with the ribosome-inactivating or the abortifacient activity of this compound. Two possible mechanisms are immediately apparent. Selective binding or uptake of GLQ 223 by infected cells could be responsible for its selective action on infected cells. Once inside the infected cells, the compound could act non-specifically, via its ribosome inactivating function. Alternatively, selectivity of the agent may arise from differential effects on viral versus cellular components, resulting in greater inhibition of viral compared to cellular nucleic acid and protein synthesis.

Lifson et al., U.S. Pat. No. 4,795,739 (issued Jan. 3, 1989), discloses that plant proteins, including trichosanthin, reduce viral antigen expression in HIV-infected cells, and are selectively toxic to HIV-infected cells. These proteins are said to be useful for treating HIV infections in humans.

The cytotoxic side effects of trichosanthin are well known (Qian, R. Q. et al., *Acta Chemica Sinica* 39:927–931 (1981); Gu, Z. et al. *Acta Chemica Sinica* 43:943–945 (1984)) since it has been used for centuries in Chinese traditional medicine, in particular for abortion and treatment of trophoblastic tumors (Li, S.C. (1596) Pen Ts'ao Kang Mu, (Chinese Pharmaceutical Compendium) reprinted by People's Medical Publishing House, Beijing (1977); Cheng, K. F., *Obstet. Gynecol.* 59:494–498 (1982); Chan, W. Y. et al., *Contraception* 29:91–100 (1984)). The cytotoxicity of GLQ 223 has also been documented in recent clinical trials in the United States (Palcca, J., *Science* 247:1406 (1990)). Thus, concerns with therapeutic safety of trichosanthin (Palcca, supra) and other plant derived agents, represent serious obstacles in their utility as anti-HIV therapeutics.

SUMMARY OF THE INVENTION

Trichosanthin is a protein isolated from *Trichosanthes kirilowii* which has been reported to have anti-HIV activity (McGrath, M. S. et al., supra). However, toxicity to normal cells has led to concerns over its clinical utility (Palcca, J., supra). It is an object of the present invention to overcome this and other aforementioned deficiencies of the prior work.

The present invention provides a protein obtainable from the root tubers of the plant *Trichosanthes kirilowii* which has potent anti-HIV activity but low toxicity, substantially free of other plant-derived contaminants, or a functional derivative thereof. The protein of the present invention, TAP 29, differs from trichosanthin in both its physico-chemical properties, amino acid sequence and, importantly, lacks the non-specific cytotoxicity of trichosanthin. The therapeutic index of TAP 29 is at least two orders of magnitude higher than that of trichosanthin.

In one embodiment, the protein is purified from the plant material; alternatively, it is produced by recombinant DNA techniques.

In a preferred embodiment, the protein, TAP 29, has a molecular weight of about 29 kD as determined by SDS polyacrylamide gel electrophoresis and has an N-terminal amino acid sequence SEQ ID No:1 (see Table 1).

The invention also provides a process for purifying a protein having anti-HIV activity from the root tuber of the plant *Trichosanthes kirilowii*, comprising:

(a) grinding the root tuber to obtain a fine powder and extracting the powder;

(b) centrifuging the extract at least once, and recovering the supernatant; and (c) fractionating the supernatant and recovering the protein.

The invention is further directed to a DNA sequence encoding the amino acid sequence of TAP 29 comprising SEQ ID No: 1, or of a functional derivative thereof, substantially free of other DNA sequences. The DNA is preferably genomic DNA or cDNA. The DNA sequence preferably comprises an expressible vehicle.

The invention also provides prokaryotic and eukaryotic host cells, including yeast, mammalian and plant cells, transformed or transfected with the above DNA.

Also provided is a substantially pure protein encoded by the DNA expressed in a prokaryotic or eukaryotic host.

Also provided is an antibody specific for TAP 29, either polyclonal, monoclonal, or chimeric.

The present invention also provides improved methods for treating a subject with an HIV-1 infection. More specifically, the invention is directed to a method for treating a subject infected with HIV-1 comprising administering to the subject an effective amount the TAP 29 protein or a functional derivative thereof.

The invention is also directed to a method for treating a subject infected with HIV-1 by administering the TAP 29 protein in combination with any one or more of the known anti-AIDS therapeutics, including, but not limited to, AZT, ddI, soluble CD4, ddC, ddA and MAP 30.

The treatment methods of the invention also includes administering to a subject infected with HIV-1 a conjugate of TAP 29 with soluble CD4, CD4 derivatives, antibodies specific for CD4, or HIV-coded glycoproteins such as gp120 and gp41.

DETAILED DESCRIPTION OF THE INVENTION

Figure 1:
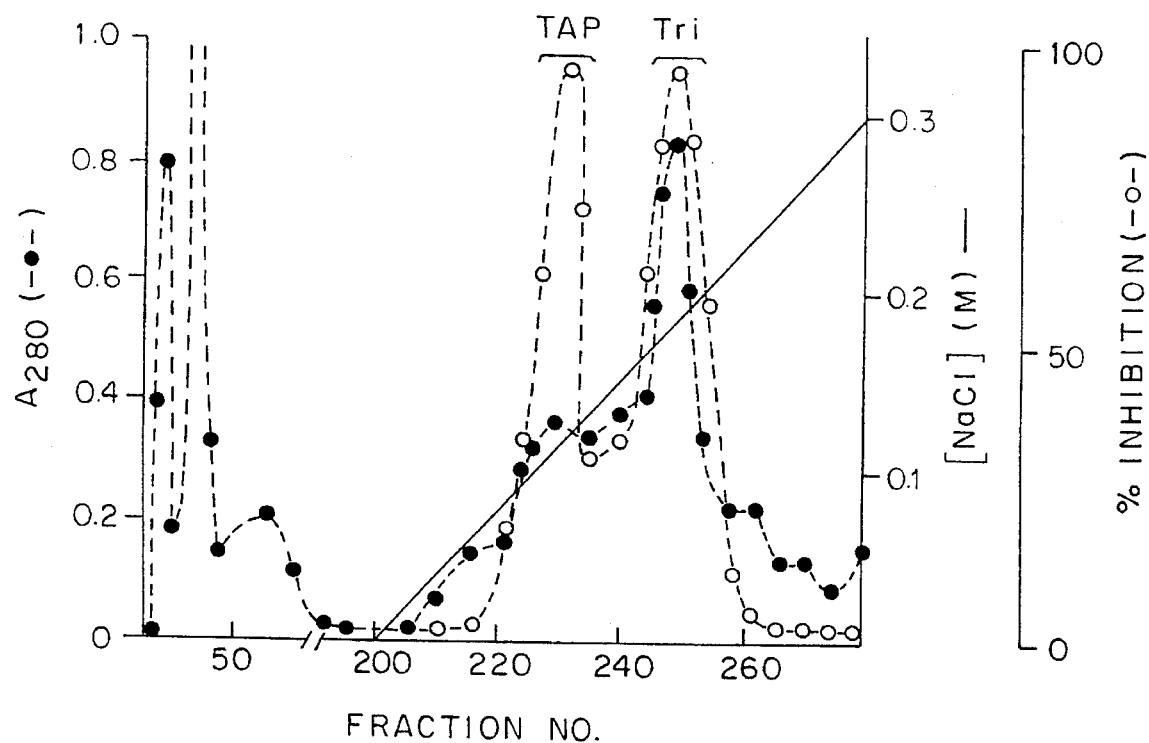
FIG. 1 is a graph depicting the purification of TAP 29 from *Trichosanthes kirilowii*. The dialyzed and concentrated sample from step (A), 20 ml containing 164 mg of protein was chromatographed on a column of CM-Sepharose CL6B as described in the text. The elution gradient is shown as a solid line. Fractions of 6 ml were collected at a flow rate of 36 ml/hr. Absorbance at 280 nm (-●-) of each fraction was measured. Ribosome-inactivating activity (-o-) was assayed with 1 µl of 1:100 dilution of the fractions. Active fractions were pooled as indicated by the horizontal bars.
Figure 2:
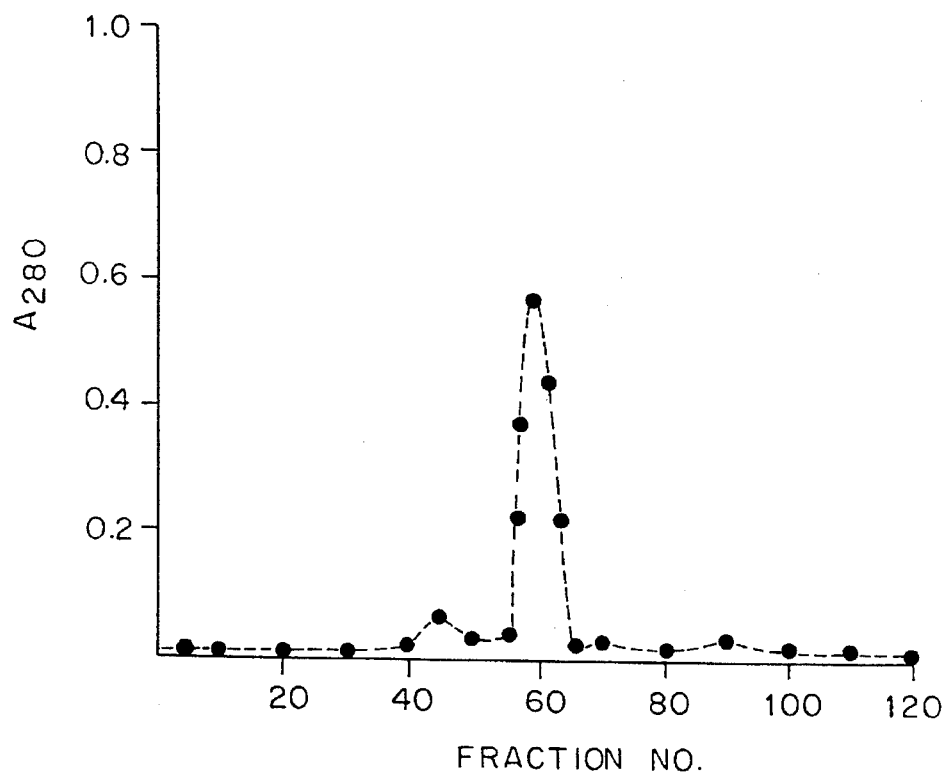
FIG. 2 is a graph depicting further purification of TAP 29 by Sephadex gel filtration. Pooled samples from the CM-Sepharose CL6B purification step were dialyzed against buffer B and concentrated to 2 ml. This material containing 5 mg of protein was applied to a column of Sephadex G75 as described in the text. Elution was carried out at 2 ml/hr. and 1 ml fractions were collected. Absorbance at 280 nm (-o-) was measured. TAP 29 was eluted as a homogeneous peak at a Ve of about 0.48 corresponding to a molecular weight of about 29 kDa.

The plant protein of the present invention, TAP 29, which is distinct from GLQ 223, belongs to the family of single chain ribosome-inactivating proteins, or SCRIPs.

The root tuber of the plant *Trichosanthes kirilowii* is the source material for the isolation of the TAP 29 protein. *T. kirilowii* grows widely in southern China, and the best medicinal quality tubers are harvested in the winter season between November and February. *T. kirilowii* has not been naturally available in the United States. In order to provide a constant and sufficient supply of the source material for the inventors' experiments, they planted and cultivated this plant. The starting material used in the present invention were root tubers harvested from plants grown in the United States.

Seeds are planted and germinated after 4–6 weeks. Plants grow fully from Spring to late Fall. Tubers are harvested in early winter for the preparation of trichosanthin and TAP 29.

TAP 29 may also be present in other related species such as *T. cucumeroides* and *T. cucumerina*.

By the term "anti-HIV activity" is intended the ability to inhibit viral attachment to cells, viral entry into cells, and cellular metabolism which permits viral replication, production and release. Also intended is the inhibition of intercellular spread of the virus. The term is meant to encompass inhibition of synthesis and cellular expression of viral antigens, activity of virus-coded enzymes such as reverse transcriptase and protease, and all known HIV pathogenic actions, such as, for example, immunosuppression. Thus, any activity which tends to inhibit any of these mechanisms is "anti-HIV activity."

The TAP 29 protein is used for treatment of HIV infection either alone, or in combination with other modes of therapy known in the art. Such modes of therapy include chemotherapy with drugs, such as AZT, ddC, ddA, ddT ddI, plant proteins such as MAP 30, or with biologically based therapy, such as, for example, soluble CD4, antibodies to CD4, and conjugates of CD4 or anti-CD4.

It is known that trichosanthin inhibits the growth of trophoblastic tumors (Cheng, K. F., supra; Chan, W.Y. et al., supra). Extracts from the root tuber of *T. kirilowii* have been used for more than 400 years to treat obstetric and gynecological diseases, restore menstruation, and facilitate the expulsion of detained placentae (Li, S.C., supra). Therefore, TAP 29 is useful for treating these and other related disorders for which trichosanthin is used, most notably due to its anti-tumor activity. By the term "anti-tumor activity" is intended the ability to inhibit the growth of tumor cells in vitro or in vivo, to inhibit the development of a tumor in vivo from a tumor cell which has undergone tumorigenic transformation in vivo in the subject animal or from a tumor cell which has been implanted in the animal. This term is intended to encompass the actual oncogenic transformation of a cell to become tumorigenic, as well as the ability of a tumor cell to metastasize to or invade an alternate site in the body.

By "functional derivative" is meant a "fragment," "variant," "analog," or "chemical derivative" of TAP 29, which terms are defined below. A functional derivative retains at least a portion of the function of TAP 29 which permits its utility in accordance with the present invention, such as anti-HIV activity.

A "fragment" of TAP 29 refers to any subset of the molecule, that is, a shorter peptide.

A "variant" of TAP 29 refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis (as exemplified by Adelman et al., *DNA* 2:183 (1983)) of nucleotides in the DNA encoding the peptide molecule, thereby producing DNA encoding the variant, and thereafter expressing the DNA in recombinant cell culture. The variants typically exhibit the same qualitative biological activity as the nonvariant peptide.

An "analog" of TAP 29 refers to a non-natural molecule substantially similar to either the entire molecule or a fragment thereof.

A "chemical derivative" of TAP 29 contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-l,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking TAP 29 or its functional derivatives to a waterinsoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980)

For routine preparation of TAP 29 according to the present invention, root tubers from *T. kirilowii* are ground into fine powder. This powder is then extracted with phosphate-buffered saline (PBS, 10 mM sodium phosphate, pH 7.6, 0.15N NaCl) by stirring gently at 4° C. overnight. For example, for powder from 60 g of root tubers, about 200 ml of PBS is used. The extract may be filtered through two layers of cheesecloth and then cleared by centrifugation at about 17,210×g for about 30 min. The supernatant is collected, dialyzed thoroughly against water, and finally against 50mM sodium phosphate buffer, pH 6.3 (buffer A). This above procedure is designated step (A).

In step (B) of the purification procedure, the dialyzed solution from step (A) is centrifuged at about 17,210×g for about 30 min to remove any precipitate formed during dialysis. The solution is concentrated using a Centriprep 10 concentrator (Amicon), for example, to 20 ml from a 200 ml starting preparation. This sample, which in a typical preparation may contain 100–200 mg of protein, is loaded onto a column of CM-Sepharose CL6B (1.5×36 cm) (Pharmacia), which was previously equilibrated with buffer A. The column is washed with the same buffer until a baseline absorbance reading is reached. The elution is monitored by UV absorption at $A_{280}$. The majority of the contaminating impurities are excluded from the column while TAP 29 and trichosanthin are retained on the column. They are eluted with a linear gradient consisting of, for example, 250 ml buffer A and 250 ml of buffer A containing 0.3M of NaCl. A typical elution profile is shown in FIG. 1 and described in detail in Example I. The fractions are then assayed for anti-HIV activity and ribosome-inactivating activity. TAP 29 is eluted at about 0.1–0.13M NaCl. Trichosanthin is eluted at between 0.15–0.18M NaCl. Trace amounts of contaminants of smaller proteins of about 11–16 kDa may be present in these fractions. The bulk of these 11–16 kDa proteins are eluted between 0.22–0.28M . From 60 g of starting plant material, the yield of TAP 29 can be in the range of 3–10 mg, preferably about 5–7 mg. The yield of trichosanthin is typically 16–24 mg. At this stage, the samples are about 75% pure. As is readily apparent to one skilled in the art, effective fractionation depends on the optimum design of the experimental conditions in terms of the capacity of the exchanger, the size of the column, the amount of the sample, and the elution conditions.

In step (C), the pooled sample of TAP 29 from step (B) is dialyzed against 20mM sodium phosphate buffer, pH 7.2 (buffer B). The precipitate formed during dialysis is removed by centrifugation at about 17,21×g for 30 min. The sample is then concentrated, for example, using a Centricon B15 concentrator (Amicon), to about 2ml, and subjected to gel filtration on Sephadex G75 superfine (Pharmacia), preferably using a column of 1.5×86 cm and buffer B. The flow rate is adjusted to about 2 ml/hr. and 1 ml fractions are collected. Homogeneous TAP 29 elutes at about 0.48 column volume, corresponding to a molecular weight of about 29 kDa. A small shoulder at the leading edge of the peak represents aggregates of this protein. The formation of aggregates during dialysis and gel filtration reduces the yield considerably. Typically 1 to 2 mg of pure soluble material is obtained from this step. The small tail peak contains the 11–16 kDa proteins, which show neither anti-HIV nor ribosomeinactivating activity.

Homogeneous samples are used for structural and functional characterization using tryptic analysis, amino acid sequencing, antibody production, and assessment of biological activity, such as inhibition of in vitro protein synthesis (ribosome inactivation), and anti-HIV activity.

Genomic and cDNA clones encoding TAP 29 from *Trichosanthes kirilowii* are cloned based on knowledge of partial amino acid sequences. Oligonucleotide primers designed from these sequences are used in the polymerase chain reaction (PCR) to specifically amplify the TAP 29 gene using two methods.

In the first method, two primers encoding two ends of the TAP 29 peptide are used in PCR with poly (A+) mRNA and genomic DNA as template. The genomic or cDNA fragment thus amplified are cloned into the plasmid pUC18, making use of restriction sites added to the 5'-end of the oligonucleotide primers. This method requires very little starting material for use as a template.

In the second method, a single specific primer is used. Lambda phage libraries generated from genomic DNA or cDNA are used as template. Using the PCR reaction to amplify specific clones is more sensitive than directly screening the plated libraries with labelled oligonucleotide. Phage DNA from the libraries is prepared from a plate lysate, and the mixture is used as a template in PCR. One of the primers is designed from the specific amino acid sequence of the SCRIP, and the other primer is complementary to the lambda phage vector near one end of the cloning site. With appropriate stringency in the PCR conditions, few specific clones should be amplified. In this method, only one specific primer is necessary.

High molecular weight genomic DNA is isolated from *Trichosanthes kirilowii*. There are several problems unique to isolation of nucleic acids from plant tissues. First, the plant cell wall is difficult to disrupt without shearing high molecular weight DNA. Second, crude plant extracts contain large quantities of polysaccharides, tannins, and pigments which copurify with nucleic acids and interfere with subsequent analysis and enzymatic manipulation.

Freshly harvested *T. kirilowii* leaves may be quick frozen in dry ice and used immediately for the preparation of genomic DNA. The frozen leaves can also be stored at −70° C. until use. Frozen tissue can be homogenized without damage to high molecular weight DNA using a mortar and pestle in liquid nitrogen. For example, for isolation of genomic DNA, 5 grams of powdered plant tissue are resuspended in a 50 ml extraction buffer consisting of 100 mM Tris HCl pH 8.0, 0.7M NaCl, 10 mM EDTA, 1% 2-mercaptoethanol, and 1% (w/v) cetyl triammonium bromide (CTAB), and incubated at 55° C. for 30 minutes. The detergent CTAB efficiently disrupts the cell wall and forms a soluble complex with nucleic acids in the presence of the high salt (0.7M NaCl). The mixture is then cooled to room temperature and extracted twice with chloroform/isoamyl alcohol. The aqueous layer is centrifuged at 4,000×g for 10 minutes, and any precipitate is discarded. The supernatant is then diluted with an equal volume of precipitation buffer, consisting of 100 mM Tris HCl pH 8.0, 10 mM EDTA, 1% CTAB, and allowed to stand at room temperature for 1 hour. As the salt concentration is reduced below 0.4M NaCl, the CTAB-nucleic acid complex precipitates, leaving the polysaccharides and other contaminants in solution. The mixture is then centrifuged at 4,000×g for 30 minutes.

The pellet is resuspended in 10 mM Tris, 1 mM EDTA (TE), and extracted twice with phenol/chloroform, and once with chloroform/isoamyl alcohol. The solution is made 0.3M with sodium acetate, and three volumes of ethanol are layered on top. Genomic DNA is spooled from the solution by stirring with a sterile glass rod. The DNA is rinsed with 70% ethanol, dried briefly, and resuspended in TE at 1 mg/ml. By agarose gel electrophoresis, the size of the DNA prepared in this way has been determined to be over 20 kb. In one preparation, for example, the yield from 1 gram of starting material was found to be about 0.2 mg of high molecular weight DNA.

RNA is prepared from these plant tissues by blending the frozen tissue in the presence of liquid nitrogen into powder, and homogenizing the powder in 10 weight volumes of RNAzol, a commercially available extraction agent which contains guanidine isothiocyanate, SDS, and phenol (Cinna/Biotecx, Texas). The homogenate is expected to contain polysaccharides, and is centrifuged at 4,000×g for 30 minutes at 4° C. The supernatant is carefully removed, leaving behind a gelatinous mass. The supernatant is extracted twice with an equal volume of chloroform; DNA and protein form an insoluble complex at the interface. RNA is precipitated from the aqueous layer with isopropanol. The pellet is resuspended, extracted with phenol:chloroform, and precipitated with ethanol to yield total cellular RNA. In one preparation from *Trichosanthes kirilowii* root tuber, for example, using this method, the yield from 1 gram of starting material was about 50 μg RNA. The $A_{260}/A_{280}$ ratio was found to be 1.9 to 2.1.

Poly (A+) RNA is isolated by chromatography on oligo-dT cellulose. Yields of 2–5% of RNA are routinely obtained.

cDNA and genomic libraries are cloned into lambda gt11 vector using established methods. Use of the EcoR1 site of gt11 offers specific advantages, as it is possible to use one primer complementary to the β-galactosidase gene adjacent to the cloning site to amplify specific clones, using another primer complementary to the specific gene, in this case, TAP 29.

cDNA synthesis was done according to the procedure of Gubler and Hoffman (Gene 25:263 (1983). First strand cDNA was synthesized using poly (A+) RNA as template and using murine Moloney leukemia virus reverse transcriptase with oligo-dT as primer. Second strand cDNA was made using DNA Polymerase I and *E. coli* ligase in the presence of RNAse H. Double-stranded cDNA is made blunt ended with T4 polymerase, and the resulting cDNA was treated with EcoR1 methylase. EcoR1 linkers were then added, and the cDNA was ligated to lambda gt11 arms and packaged into phage.

Genomic DNA was partially digested with MboI and size-selected for fragments of 15–23 kb by preparative agarose gel electrophoresis. These fragments were then made blunt-ended, treated with EcoR1 methylase, and cloned into lambda gt11 with EcoR1 linkers.

Oligonucleotide primers for PCR are designed from the amino acid sequence of TAP 29. Because the degeneracy of the genetic code increases the number of possible codon choices at each position, in order to account for every possibility, a mixture of oligonucleotide primers is used. One of these primers is exactly complementary to the gene in that region. Alternatively, the primers are made longer, and each possibility is not accounted for. In this latter case, the length of the primer and the first two bases of each codon confer the specificity required. Although the exact complement of the gene is not present, the primer is sufficiently specific for use in the PCR.

The preferred primers have a length of about 14 to about 20 nucleotides, initially, with degeneracy of 1024 or less. A hexanucleotide containing a restriction fragment recognition site, such as HindIII, is added to the 5'-end of the primers for use in cloning.

The following 14-base oligonucleotide primer/probe has been designed based on the N-terminal amino acid sequence unique to TAP 29. This oligonucleotide has a degeneracy of 32:

```
Residue Lys  —Lys  —Lys  —Val  —Tyr
     5' AAA—AAA—AAA—GTT—TA  3'  (SEQ ID NO:3:)
        G    G    G    A
                       C
                       G 3' TTT—TTT—TTT—CAA—AT  5'
        C    C    C    T
                       G
                       C
```

The following 24-base oligonucleotides complementary to the β-galactosidase gene near the EcoR1 cloning site have been used as primers in PCR:

Lambda 1  5' GGTGGCGACGACTCCTGGAGCCCG 3'
Lambda 2  5' TTGACACCAGACCAACTGGTAATG 3'

In conjunction with a single sequence-specific primer, these lambda primers have been used to amplify specific clones from genomic and cDNA libraries, as well as to obtain overlapping clones which encode areas outside of known nucleotide sequences. Oligonucleotides are synthesized using an Applied Biosystems 380B synthesizer using the phosphorimidate method, and purified using HPLC. A 5' phosphate group is added using T4 kinase.

Using the two primer approach, both oligonucleotides are designed to encode separate portions of the TAP 29 peptide. The template is either genomic DNA or cDNA. Using the one primer method, the other primer is a lambda primer and the template is a mixture of phage DNA isolated from the libraries.

Reviews of the polymerase chain reaction are provided by Mullis, K. B. (*Cold Spring Harbor Symp. Quant. Biol.* 51:263–273 (1986)); Saiki, R. K., et al. (*Bio/Technology* 3:1008–1012 (1985)); and Mullis, K. B., et al. (M*et. Enzymol.* 155:335–350 (1987)).

PCR reaction condition variables include annealing temperature, polymerization time, and ratio of template to primers. In one embodiment, 100 ng of cDNA or 1 µg of total genomic DNA or mixed phage library DNA is used as template. Then, 5–100 pmol of oligonucleotide primer is used, depending upon the degeneracy of the primer. PCR reactions are carried out in a programmable thermal cycler.

A typical cycle consists of 94° C. denaturation for 1 minute, 45° C. annealing for 2 minutes, and 72° C. polymerization for 3 minutes for the first 20 cycles, followed by an additional 20 cycles during which the polymerization time is incrementally increased by two seconds each cycle. Reaction products are analyzed by agarose gel electrophoresis using conventional agarose for products 500 bp to several kilobases, and NuSieve agarose for products 100 bp to 2 kb.

The genomic or cDNA fragment thus amplified is cloned making use of restriction sites added to the 5'-end of the oligonucleotide primers. The PCR reaction products are digested with restriction enzyme, and cloned into a pUC18 vector which has been linearized at the appropriate site and treated with calf intestinal phosphatase. These clones are then screened using radiolabelled gel-purified DNA corresponding to the major PCR products.

These clones are used to screen genomic and cDNA lambda phage libraries for overlapping clones. In addition, sequence information from these clones is used to design new primers for single-primer PCR amplification from phage libraries. Alternatively, primer extension using sequences derived from these clones is used to generate full length cDNA clones.

Techniques for synthesizing such oligonucleotides are also disclosed by, for example, Wu, R., et al., *Prog. Nucl. Acid. Res. Molec. Biol.* 21:101–141 (1978)). Procedures for constructing recombinant molecules in accordance with the above-described methods are disclosed by Sambrook, J. T. et al., *Molecular Cloning: A Laboratory Manual*, Second Ed., Cold Spring Harbor Press, Cold Spring Harbor, N.Y. (1984). These two references are herein incorporated by reference.

The cloned genes for TAP 29 can be expressed in prokaryotic expression vectors or in eukaryotic expression vectors, which are known in the art.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing the plant protein of the invention in order to produce a prokaryotic genomic expression vector library. Procedures for preparing cDNA and for producing a genomic library are disclosed by Sambrook et al., (supra).

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-noncoding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3' region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a sequence encoding the desired protein) are said to be "operably linked" if the nature of the linkage between the two DNA sequences does not (1) result in the introduction of a frame-shift mutation, (2) interfere with the ability of the promoter region sequence to direct the transcription of the gene to be expressed, or (3) interfere with the ability of the gene sequence which is to be expressed to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

A promoter is a double-stranded DNA or RNA molecule which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. A "promoter sequence complement" is a nucleic acid molecule whose sequence is the complement of a "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement").

Certain RNA polymerases exhibit a high specificity for such promoters. The RNA polymerases of the bacteriophages T7, T3, and SP-6 are especially well characterized, and exhibit high promoter specificity. The promoter sequences which are specific for each of these RNA polymerases also direct the polymerase to utilize (i.e. transcribe) only one strand of the two strands of a duplex DNA template. The selection of which strand is transcribed is determined by the orientation of the promoter sequence. This selection determines the direction of transcription since RNA is only polymerized enzymatically by the addition of a nucleotide 5' phosphate to a 3' hydroxyl terminus.

The promoter sequences of the present invention may be either prokaryotic, eukaryotic or viral. Suitable promoters are repressible, or, more preferably, constitutive. Examples of suitable prokaryotic promoters include promoters capable of recognizing the T4 (Malik, S. et al., *J. Biol. Chem.* 263:1174–1181 (1984), Rosenberg, A. H. et al., *Gene* 59:191–200 (1987); Shinedling, S. et al., *J. Molec. Biol.* 195:471–480 (1987); Hu, M. et al., *Gene* 42:21–30 (1986)), T3, Sp6, and T7 (Chamberlin, M. et al., *Nature* 228:227–231 (1970); Bailey, J. N. et al., *Proc. Natl. Acad. Sci. (U.S.A.)* 80:2814–2818 (1983); Davanloo, P. et al., *Proc. Natl. Acad. Sci. (U.S.A.)*. 81:2035–2039 (1984)) polymerases; the $P_R$ and $P_L$ promoters of bacteriophage 1 (*The Bacteriophage Lambda*, Hershey, A. D., Ed., Cold Spring Harbor Press, Cold Spring Harbor, N.Y. (1973); *Lambda II*, Hendrix, R. W., Ed., Cold Spring Harbor Press, Cold Spring Harbor, N.Y. (1980)); the trp, recA, heat shock, and lacZ promoters of *E. coli*; the aamylase (Ulmanen, I., et al., *J. Bacteriol.* 162:176–182 (1985)) and the s-28-specific promoters of *B. subtilis* (Gilman, M. Z., et al., *Gene* 32:11–20 (1984)); the promoters of the bacteriophages of Bacillus (Gryczan, T. J., In: *The Molecular Biology of the Bacilli*, Academic Press, Inc., New York (1982)); Streptomyces promoters (Ward, J. M., et al., *Mol. Gen. Genet.* 203:468–478 (1986)); the int promoter of bacteriophage lambda; the bla promoter of the β-lactamase gene of pBR322, and the CAT promoter of the chloramphenicol acetyl transferase gene of pPR325, etc. Prokaryotic promoters are reviewed by Glick, B. R., (*J. Ind. Microbiol.* 1:277–282 (1987)); Cenatiempo, Y. (*Biochimie* 68:505–516 (1986)); Watson, J. D . et al. (In: *Molecular Biology of the Gene*, Fourth Edition, Benjamin Cummins, Menlo Park, Calif. (1987)); and Gottesman, S. (*Ann. Rev. Genet.* 18:415–442 (1984)).

Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature (London)* 290:304–310 (1981)); and the yeast gal4 gene promoter (Johnston, S. A., et al., *Proc. Natl. Acad. Sci. (USA)* 79:6971–6975 (1982); Silver, P. A., et al., *Proc. Natl. Acad. Sci.* (USA) 81:5951–5955 (1984)). All of the above listed references are incorporated by reference herein.

Production of TAP 29 or functional derivatives thereof in insects can be achieved, for example, by infecting the insect host with a baculovirus engineered to express the gene of interest by methods known to those of ordinary skill in the art. Thus, in one embodiment, sequences encoding TAP 29 may be operably linked to the regulatory regions of the viral polyhedrin protein (Jasny, *Science* 238: 1653 (1987)). Infected with the recombinant baculovirus, cultured insect cells, or the live insects themselves, can produce the TAP 29 protein in amounts as great as 20 to 50% of total protein production. When live insects are to be used, caterpillars are presently preferred hosts for large scale protein production according to the invention.

Plant cell expression systems may be particularly useful for expression of the TAP 29 protein and derivatives of the present invention, in particular if there is a requirement for plant-specific amino acids in the TAP 29 sequence that are unavailable in bacterial or animal cell expression systems. Methods for culturing plants cells and for transferring genes into such cells and expressing these genes are well-known in the art. See: *Methods for Plant Molecular Biology*, Academic Press, New York, 1988, which is hereby incorporated by reference. (The following references refer to pages in the above book). Plant cells may be grown as callus-derived cultures (Smith, R. H., pp. 343–353) and prepared as protoplasts (Potrykus, I. et al., pp. 355–383). Methods for fusion and transformation of plant protoplasts are provided by Power, J. B. et al. (pp. 385–401). Gene transfer may be achieved using Ti plasmid vectors (Rogers, S. G. et al., pp. 423–436) or plant virus vectors, such as cauliflower mosaic virus (Brisson, N. et al., pp. 437–446). Alternatively, DNA may be directly transferred into protoplasts, according to methods described by Paszkowski, J. et al. (pp. 447–460).

Expression of the cloned genes encoding the TAP 29 protein and functional derivatives of this invention permits the large scale production of the active proteins or functional derivatives. New chimeric molecules can then be created with enhanced biological or therapeutic activity, such as anti-HIV activity, and less toxicity to the host cells, using only the parts of the molecule that are active against virus-infected cells or tumor cells. For example, the TAP 29 or a portion thereof may be coupled to other proteins having inhibitory and cytotoxic properties, including, but not limited to Ricin A chain, Pseudomonas toxin, Diphtheria toxin, and tumor necrosis factor. Toxins conjugated to antibodies or other ligands, are known in the art (see, for example, Olsnes, S. et al., *Immunol. Today* 10:291–295 (1989)). Such coupling may be achieved by chemical means or by recombinant DNA techniques wherein DNA encoding TAP 29 is linked with DNA encoding another toxic protein, a CD4 molecule or fragment, a monoclonal antibody chain or fragment, such as the heavy chain variable region, and the like.

SCRIPs such as TAP 29 inhibit protein synthesis by hydrolytic cleavage of a glycosidic linkage between the adenine and the ribose at a specific site A4324 on the 28S rRNA, leaving the phosphodiester bonds of the RNA backbone intact. This reaction results in a decrease in the stability of the RNA and renders it sensitive to aniline treatment at pH 4.5, with a fragment of about 450 nucleotides being liberated on cleavage. These same results were observed with treatment of either native ribonuclear protein particles, or naked 28S rRNA. This direct interaction of SCRIPs with naked rRNA affects the stability of cellular RNA upon SCRIP treatment.

Additional conjugates of TAP 29 or a functional derivative thereof, contemplated within the scope of the present invention, include conjugates with antibodies specific for HIV antigens, such as gp120 or gp41 (Matsushita, S. et al.,

*AIDS Res. Hum. Retroviruses* 6:193–203 (1990), which is hereby incorporated by reference), conjugates with CD4 molecules or soluble CD4 fragments, and the like, and conjugates with antibodies specific for tumor antigens. Such conjugates will allow the targeted delivery of TAP 29 to a site of interest, such as a cell expressing an HIV antigen, to achieve even greater specificity and lower nonspecific toxicity.

In other embodiments, TAP 29 or an active fragment or derivative thereof, can be conjugated to a hormone, and used therapeutically to treat a tumor having a receptor for that hormone, or to specifically eliminate cells which bind that hormone. This targeted elimination of unwanted cells is based on the inhibitory activity of TAP 29 for protein synthesis, coupled with the specific targeting provided by the hormone for cells bearing appropriate hormone receptors. Thus, for example, prostate cancer, currently treated with analogs of a gonadotrophin releasing hormone (GHRH), can be treated using TAP 29 conjugated to GnRH. Acromegaly results from overproduction of growth hormone by somatotrophic cells of the anterior pituitary, which are responsive to the hypothalamic releasing hormone, growth hormone releasing hormone (GHRH). Thus, according to the present invention, TAP 29 conjugated to GHRH can be used to treat acromegaly. Similarly, Cushing's disease results from overproduction of adrenocorticotrophin by corticotrophic cells of the anterior pituitary which respond to stimulation by corticortrophin releasing hormone (CRH). According to the present invention, TAP 29 conjugated to CRH can be used to treat Cushing's disease. In general, a TAP 29-conjugated releasing hormone is useful for treating a pituitary adenoma having cells with specific receptors for the releasing hormone. (For review of endocrine and neuroendocrine hormones and receptors, see Williams, R. H., ed., *Textbook of Endocrinology*, Sixth Ed., Saunders, Philadelphia, Pa., 1981; Krieger, D. T. et al., eds., *Neuroendocrinology*, Sinauer Associates, Sunderland, Mass., 1980; and Norman, A. W. et al., eds., *Hormones*, Academic Press, New York, N.Y., 1987), which references are hereby incorporated by reference).

The present invention also provides a method for recombinant engineering of the cells of an AIDS patient for in situ expression of TAP 29. A hybrid plasmid containing the TAP 29 gene or a fragment thereof under the direction of the HIV LTR may be inserted into a retroviral vector. For a discussion of the methods involved in retroviral vector production and expression, see, for example, Palmer, T. D. et al., *Proc. Nat'l. Acad. Sci. USA* 84:1055–1059 (1987); Wilson, J. M. et al., *Proc. Nat'l. Acad. Sci. USA* 85:3014–3018 (1988); Zwiebel, J. A. et al., *Science* 243:220–222 (1989), which references are hereby incorporated by reference). Transfected cells containing an integrated HIV-TAP 29 plasmid would express very low levels of TAP 29 constitutively; however, upon transactivation with HIV infection, production of TAP 29 would be efficiently induced. The continuous presence of TAP 29, endogenously supplied, may have therapeutic benefits beyond those achieved by conventional administration of the protein.

To treat patients with HIV infection according to the present invention, TAP 29, or a functional derivative thereof, is administered to a patient in daily doses ranging from about 1 ng to about 50 mg, more preferably in a range of about 1 µg to about 10 mg. The optimum dosage can best be determined by the practitioner, based in part upon the patient's condition, weight, and response to treatment.

Alternatively, the TAP 29 or a functional derivative thereof is administered as above alternating with MAP 30 in the same dosages. This latter combined treatment should be effective in minimizing the immune response of the subject to either protein since the two proteins are immunologically distinct.

It is understood that the dosage of TAP 29 and functional derivatives thereof will be dependent upon the age, sex, health, and weight of the recipient, kind of concurrent treatment, if any, frequency of treatment, and the nature of the effect desired. The ranges of effective doses provided herein are not intended to limit the inventors and represent preferred dose ranges. However, the most preferred dosage will be tailored to the individual subject, as is understood and determinable by one of ordinary skill in the art without undue experimentation.

Alternatively, a subject with HIV infection or with AIDS is treated with the above amounts of plant proteins in conjunction with other known therapeutics, including, but not limited to, AZT, ddI, ddA, ddC, or soluble CD4. Preferably, the drugs are administered on alternate days in the recommended amounts of each drug.

TAP 29 is administered in compositions including compositions wherein the plant protein is contained in an effective amount to achieve its intended purpose. Determination of the effective amounts is well within the skill in the art.

The TAP 29 protein or pharmaceutical compositions of the present invention may be administered by any means that achieve their intended purpose. For example, administration may be by parenteral routes, including subcutaneous, intravenous, intradermal, intramuscular, intraperitoneal, intrathecal, transdermal, or buccal routes. Alternatively, or concurrently, administration may be by the oral or rectal route. The proteins and pharmaceutical compositions can be administered parenterally by bolus injection or by gradual perfusion over time.

In addition to TAP 29 or functional derivative thereof, these pharmaceutical compositions may contain suitable pharmaceutically acceptable carriers comprising excipients and auxiliaries which facilitate processing of the active compounds into preparations which can be used pharmaceutically. Preferably, the preparations, particularly those which can be administered orally and which can be used for the preferred type of administration, such as tablets, dragees, and capsules, and also preparations which can be administered rectally, such as suppositories, as well as suitable solutions for administration by injection or orally, contain from about 0.1 to about 99 percent, preferably from about 25–85 percent, of active compound(s), together with the excipient.

The pharmaceutical compositions of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding a resulting mixture and processing the mixture of granules, after adding suitable auxiliaries, if desired or necessary, to obtain tablets or dragee cores.

Suitable excipients are, in particular, fillers such as sugars, such as lactose, sucrose, mannitol, or sorbitol; cellulose preparations and/or calcium phosphates, such as tricalcium phosphate or calcium hydrogen phosphate; as well as binders such as starch paste made using, for example, maize starch, wheat starch, rice starch, potato starch, gelatin, gum tragacanth, methyl cellulose, hydroxypropylmethylcellulose, sodium carboxymethyl cellulose, and/or polyvinylpyrrolidone.

If desired, disintegrating agents may also be added, such as the above-mentioned starches as well as carboxymethyl starch, cross-linked polyvinyl pyrrolidone, agar, or alginic acid or a salt thereof, such as sodium alginate.

Auxiliaries which can be used in the compositions according to the present invention include flow-regulating agents and lubricants such as silica, talc, stearic acid or salts thereof, and/or polyethylene glycol.

Dragee cores are provided with suitable coatings which, if desired, are resistant to gastric juices. For this purpose, concentrated sugar solutions may be used, which may optionally contain gum arabic, talc, polyvinyl pyrrolidone, and the like.

Also included within the scope of the present invention is an antibody specific for TAP 29 or specific for a functional derivative thereof.

The term "antibody" refers both to monoclonal antibodies which are a substantially homogeneous population and to polyclonal antibodies which are heterogeneous populations. Polyclonal antibodies are derived from the sera of animals immunized with an antigen. Monoclonal antibodies (mAbs) to specific antigens may be obtained by methods known to those skilled in the art. See, for example Kohler and Milstein, *Nature* 256:495–497 (1975) and U.S. Pat. No. 4,376,110. Such antibodies may be of any immunoglobulin class including IgG, IgM, IgE, IgA, IgD and any subclass thereof.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316-325 (1983)).

It will be appreciated that Fab and F(ab')$_2$ and other fragments of the antibodies useful in the present invention may be used for the detection and quantitation of TAP 29 in the same manner as an intact antibody. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopic determinants usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively or qualitatively detect the presence of TAP 29. For example, it would be of benefit to monitor the level of TAP 29 in the circulation or in the tissues of a subject receiving therapeutic doses of the protein. Thus, the antibodies (of fragments thereof) useful in the present invention may be employed histologically to detect or visualize the presence of TAP 29.

An assay for TAP 29 typically comprises incubating a biological sample from the subject in the presence of a detectably labeled antibody or antibody fragment capable of identifying TAP 29 and detecting the antibody which is bound in the sample.

Thus, in this aspect of the invention, a biological sample may be treated with nitrocellulose, or other solid support which is capable of immobilizing cells, cell particles or soluble proteins. The support may then be washed with suitable buffers followed by treatment with the detectably labeled TAP 29-specific antibody. The solid phase support may then be washed with the buffer a second time to remove unbound antibody. The amount of bound label on said solid support may then be detected by conventional means.

By "solid phase support" or "carrier" is intended any support capable of binding antigen or antibodies. Wellknown supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody.

The binding activity of an anti-TAP 29 antibody may be determined according to well known methods, such as enzyme immunoassay (EIA) or radioimmunoassay (RIA). Those skilled in the art will be able to determine operative and optimal assay conditions for each determination by employing routine experimentation.

For EIA, the antibody is detectably labeled by linking to an enzyme. This enzyme, in turn, when later exposed to its substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the antibody or fragments, it is possible to detect binding to TAP 29 through the use of a RIA. A good description of RIA may be found in *Laboratory Techniques and Biochemistry in Molecular Biology*, by Work, T. S., et al., North Holland Publishing Company, NY, 1978). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA) .

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The following examples are intended to be illustrative, but not to limit, the invention.

EXAMPLE I

Preparation and Chemical Characterization of TAP 29

Root tuber of *Trichosanthes kirilowii* was the source material for the preparation of TAP 29 and trichosanthin. Fresh and dried *T. kirilowii* root tubers were supplied by American Biosciences. Chromatographic materials were obtained from Pharmacia-LKB.

The homogeneity, size, and subunit structure of TAP 29 and trichosanthin were determined by SDS-PAGE (7) in the presence and absence of 2-mercaptoethanol. The chemical composition of these compounds was determined by N-terminal amino acid sequencing. Amino acid sequencing was carried out by automated Edman degradation using an Applied Biosystems model 470A protein sequencer, with on-line PTH analyzer.

Step (A): Initial Extraction

For routine preparation, 60g of root tubers from *T. kirilowii* were ground into fine powder. This powder was then extracted with 200 ml of a phosphate-buffered saline (PBS, 10 mM sodium phosphate, pH 7.6, 0.15N NaCl) by stirring gently at 4° C. overnight. The extract was first filtered through two layers of cheesecloth and then cleared by centrifugation at 12,000×g for 30 min. The supernatant was collected, dialyzed thoroughly against water, and finally against 50mM sodium phosphate buffer, pH 6.3 (buffer A).

Step (B): CM-Sepharose CL6B

The dialyzed solution from step (A) was centrifuged at 17,210×g for 30 min to remove any precipitate formed during dialysis. The solution was concentrated using a Centriprep 10 concentrator (Amicon) to 20 ml. This sample containing 164 mg of protein was loaded onto a column of CM-Sepharose CL6B (1.5×36 cm), which was previously equilibrated with buffer A. The column was washed with the same buffer until the baseline absorbance reading of $A_{280}$ nm was reached. The majority of the contaminating impurities were excluded from the column while TAP 29 and trichosanthin were retained on the column. The proteins were eluted with a linear gradient consisting of 250 ml buffer A and 250 ml of buffer A containing 0.3M NaCl. A typical elution profile is shown in FIG. 1. The fractions were assayed for anti-HIV activity and ribosome-inactivating activity (see below). TAP 29 was eluted at about 0.1–0.13M NaCl. Trichosanthin was eluted at between 0.15–0.18M NaCl. Trace amounts of contaminants of lower molecular weight proteins of about 11–16 kDa were present in these fractions. The bulk of the 11–16 kDa proteins were eluted between 0.22–0.28M. The yield of TAP 29 and trichosanthin was usually about 5–7 mg and 16–24 mg respectively. At this stage, the samples were about 75% pure.

Step (C): Sephadex G 75 Gel Filtration

The pooled sample of TAP 29 from step (B) was dialyzed against 20 mM sodium phosphate buffer, pH 7.2 (buffer B). The precipitate formed during dialysis was removed by centrifugation. The sample was then concentrated using a Centricon B15 concentrator (Amicon) to a volume of about 2 ml, and subjected to gel filtration on Sephadex G75 superfine. A column of 1.5×86 cm in buffer B was used in this case. The flow rate was adjusted to 2 ml/hr. and 1 ml fractions were collected. Homogeneous TAP 29 was eluted at about 0.48 column volume, corresponding to a molecular weight of about 29 kDa. A small shoulder at the leading edge of the peak represents aggregates of this protein. The formation of aggregates during dialysis and gel filtration reduces the yield considerably. Typically 1 to 2 mg of pure soluble material is obtained from this step. The small tail peak contains the 11–16 kDa proteins, which show neither anti-HIV nor ribosome-inactivating activity.

Physical Characterization

Figure 3A:
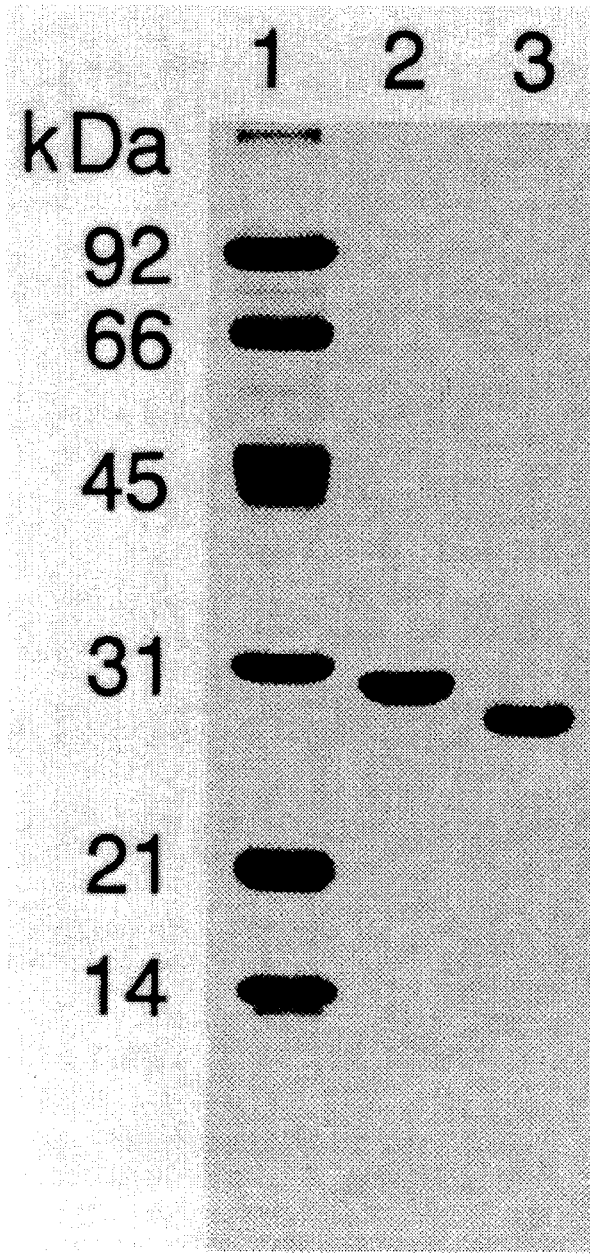
FIGS. 3A and 3B depict a gel pattern showing SDS-polyacrylamide gel electrophoresis (SDS-PAGE) of samples of TAP 29 purified as shown in FIGS. 1 and 2. Electrophoresis was carried out in the presence FIG. 3A and absence FIG. 3B of the reducing agent 2-mercaptoethanol in 10% acrylamide at a constant voltage of 90 V for 5 hr, until the bromophenol blue tracking dye reached 1 cm from the lower edge of the gel. The gels were stained with silver stain. A: Samples treated with 2-mercaptoethanol, lane 1, molecular weight standards, 2 µg each; lanes 2 and 3, TAP 29 and trichosanthin, 3 µg each. B: Samples without 2-mercaptoethanol treatment, lane 1, TAP 29 1.5 µg; lane 2, molecular weight standards, 2 µg each, and lane 3, trichosanthin, 1.5 µg.
Figure 3B:
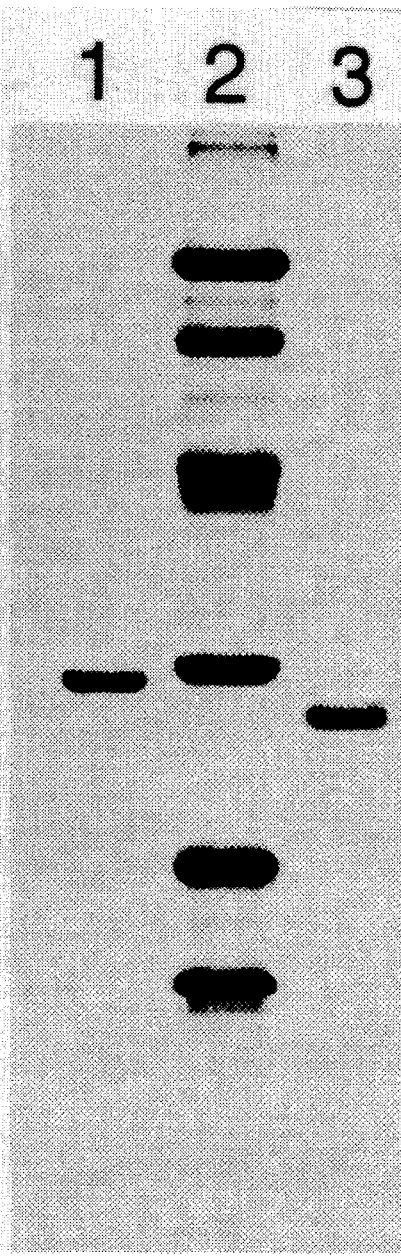

The size, homogeneity, and subunit structure of TAP 29 and trichosanthin as determined by SDS-PAGE are shown in FIG. 3. Single bands with MW of 29 kDa and 26 kDa were obtained for TAP 29 and trichosanthin respectively, both in the presence and absence of the reducing agent, indicating that these proteins are single chain polypeptides.

EXAMPLE II

N-TERMINAL AMINO ACID SEQUENCE OF TAP 29

The N-terminal amino acid sequence of TAP 29 was determined by automated Edman degradation using an Applied Biosystems model 470A protein sequencer, with on-line PTH analyzer.

The sequence of the first 44 amino acids from the N-terminus of TAP 29 is shown in Table 1 (SEQ ID:NO. 1). It is different from the corresponding sequence of trichosanthin (SEQ ID:NO:2), as determined by the present inventors and also reported by others (Zhang, X. et al., *Nature* 321:477–478 (1986); Maraganore, J. M.et al., *J. Biol. Chem.* 262:11628–11633 (1987); Collins, E. J. et al., *J. Biol. Chem.* 265:8665–8669 (1990); and Chow, T. P. et al., *J. Biol. Chem.* 265:8670–8674 (1990)). In addition to three conservative substitutions at position 29 (Arg to Lys), position 37 (Ile to Val), and position 42 (Pro to Ser, a stretch of five amino acids from position 12 to 16 (SEQ ID:NO. 1) is distinct in TAP 29. This sequence is Lys-Lys-Lys-Val-Tyr, whereas the corresponding sequence in trichosanthin (SEQ ID:NO.2) is Ser-Ser-Tyr-Gly-Val. This difference in sequence results in three potential tryptic sites in TAP 29 not found in trichosanthin. These three tryptic sites would give two meaningful tryptic fragments and a free lysine.

Interestingly, the corresponding sequence in MAP 30, another nontoxic anti-HIV protein discovered by the present inventors is similar to the TAP 29 sequence (Lee-Huang, S. et al., *FEBS Lett.* 272:12–18 (1990)), also providing two potential tryptic sites.

Such sequences are not found in trichosanthin or ricin A chains, all of which are toxic to intact cells. The role of these tryptic sites and the positively charged lysine residues in determining cytotoxicity is thought to be important and awaits study by site-specific mutation and modification of these proteins.

TABLE 1

N-terminal Amino Acid Sequence of TAP 29
Comparison with trichosanthin

|  | 1 | | | | | | | | | 10 |
|---|---|---|---|---|---|---|---|---|---|---|
| TAP 29 | Asp | Val | Ser | Phe | Arg | Leu | Ser | Gly | Ala | Thr |
| Tri | Asp | Val | Ser | Phe | Arg | Leu | Ser | Gly | Ala | Thr |
|  | 11 | | | | | | | | | 20 |
| TAP 29 | Ser | Lys | Lys | Lys | Val | Tyr | Phe | Ile | Ser | Asn |
| Tri | Ser | Ser | Ser | Tyr | Gly | Val | Phe | Ile | Ser | Asn |
|  | 21 | | | | | | | | | 30 |
| TAP 29 | Leu | Arg | Lys | Ala | Leu | Pro | Asn | Glu | Lys | Lys |
| Tri | Leu | Arg | Lys | Ala | Leu | Pro | Asn | Glu | Arg | Lys |
|  | 31 | | | | | | | | | 40 |
| TAP 29 | Leu | Tyr | Asp | Ile | Pro | Leu | Val | Arg | Ser | Ser |
| Tri | Leu | Tyr | Asp | Ile | Pro | Leu | Ile | Arg | Ser | Ser |
|  | 41 | | | | 45 | | | | | |
| TAP 29 | xxx | Ser | Gly | Ser | Lys | | | | | |
| Tri | Leu | Pro | Gly | Ser | | | | | | |

Comparison of the N-terminal 44 residues of TAP 29 to that of trichosanthin (Tri). Underlined regions are unique amino acids of TAP 29.

EXAMPLE III

Anti-HIV Activity of TAP 29

The anti-HIV activity of TAP 29 was measured by microtiter syncytia formation in infectious cell center assay (Nara, P. L. et al., *Nature* 332:469–470 (1988)), viral core protein p24 expression (Nara, P. L. et al., *AIDS Res. Human Retroviruses* 3:283–302 (1987)), and viral associated RT activity (Hoffman, A. D. et al., *Virology* 147:326–335 (1985)). Only specific experimental conditions will be discussed herein.

CEM-ss (syncytium sensitive, CD4 and Leu-3 positive) cell line was used as the indicator cells for the microtiter syncytial-forming assay. The H9 cell line was used for p24 expression and viral-associated RT activity assays in suspension cultures. HIV-1 virus was prepared and stocked as described previously (Nara et al., 1988, supra). The cell lines were maintained in RPMI-1640 complete medium which contains 100 U/ml of penicillin-streptomycin and 10% heat-inactivated fetal calf serum.

Microtiter Syncytia Formation Assay

This assay is based on the interaction between fusigenic virus-infected cells expressing the HIV envelope gene products and uninfected adjacent cells bearing CD4 molecules. It quantitates acute cell-free HIV-1 infection.

Freshly prepared indicator cells in complete medium at $5 \times 10^4$ in 100 µl were treated with 100 µl of TAP 29 or trichosanthin at various concentration (see Table 2) for 90 min. At the end of this time, 100 µl of frozen pre-titrated HIV stock from HxB3/H9 cells, corresponding to 100–300 syncytial forming units (SFU) were added for 60 min. The supernatant containing anti-HIV protein and virus was then removed and the cells were washed with complete medium to remove residual free drug and virus. The cells were then plated onto poly L-lysine coated microtiter wells with 200 µl of complete medium containing drug at the same original concentration. The plates were incubated at 37° C. in a humidified incubator in an atmosphere of 5% CO2. Focal syncytium formation representing single infectious virion units was scored at day 5 by examination under an inverted microscope.

Inhibition of Syncytium Formation

The effects of TAP 29 on the infectivity of HIV-I was measured by the microtiter syncytia formation infectivity assay (Nara et al., 1988, supra). The results of two independent experiments are summarized in Table 2. A 90 minute pre-incubation of the indicator cells with TAP 29 resulted in a dose-dependent inhibition of HIV-1 infection and replication. At 0.344 and 34.4 nM, TAP 29 caused 51% and 100% inhibition of syncytial formation respectively. An $ID_{50}$ of 0.34 nM was estimated from these results. No cytotoxicity of TAP 29 was observed at these concentrations (see below). At 0.34 nM, the $ID_{50}$ of TAP 29, trichosanthin caused only 21% inhibition of syncytia formation. In sharp contrast, trichosanthin exhibited significant toxic effects on the indicator cells at concentrations above 1.5 nM (see below).

TABLE 2

Effects of TAP 29 and Trichosanthin on HIV Infection

| Conc | Syncytia/well | | % ICC (Vn/Vo) | | Cytotoxicity | |
|---|---|---|---|---|---|---|
| nM | TAP29 | Tri | TAP29 | Tri | TAP29 | Tri |
| 0 | 260 | 260 | 100 | 100 | – | – |
| 0.344 | 128 | 205 | 49 | 79 | – | – |
| 1.724 | 90 | xx | 35 | xx | – | + |
| 3.44 | 65 | xx | 25 | xx | – | + |
| 17.24 | 38 | xx | 15 | xx | – | + |
| 34.4 | 0 | xx | 0 | xx | – | + |

Values given in this table are averages of triplicates from two independent experiments. % ICC (infectious cell centers) are average number of syncytia in a drug-treated group (Vn) as a percentage of the average number of syncytia in an untreated sample (the 0 nM group). For determination of cytotoxicity of the plant proteins, triplicate cultures of indicator cells received the indicated concentration of TAP 29 or trichosanthin (Tri) at each concentration in the absense of added virus. Where cytotoxicity caused by the drug did not allow the scoring of syncytia, an "xx" is indicated.

Viral Core Protein p24 and HIV-RT Assays

The effect of TAP 29 on the in vitro replication and transmission of HIV-I was measured by p24 expression and HIV-RT activity. H9 cells were inoculated with viral stock at a multiplicity of infection of $5 \times 10^{-3}$. Cells at $5 \times 10^7$/ml were incubated with the inoculum at 37° C. for 60 min. to allow viral absorption. Unbound virus was removed by washing with medium. The cells were then resuspended in complete medium and plated at $1 \times 10^5$/ml in the presence or absence of TAP 29 for the duration of the experiment. Under the assay conditions, viral production peaks at day 4. Cells were thus harvested at this time, and cell-free supernatants were collected for the determination of p24 production and HIV-RT activity. p24 was assayed by RIA and expressed in ng/ml (Nara et al., 1987, supra). HIV-RT activity was measured by the incorporation of [$^3$H]thymidine with poly(rA).poly(dT)12–18 as primer-template, and the results are expressed in cpm/ml.

Inhibition of Viral Core Protein p24 Expression

Figure 5:
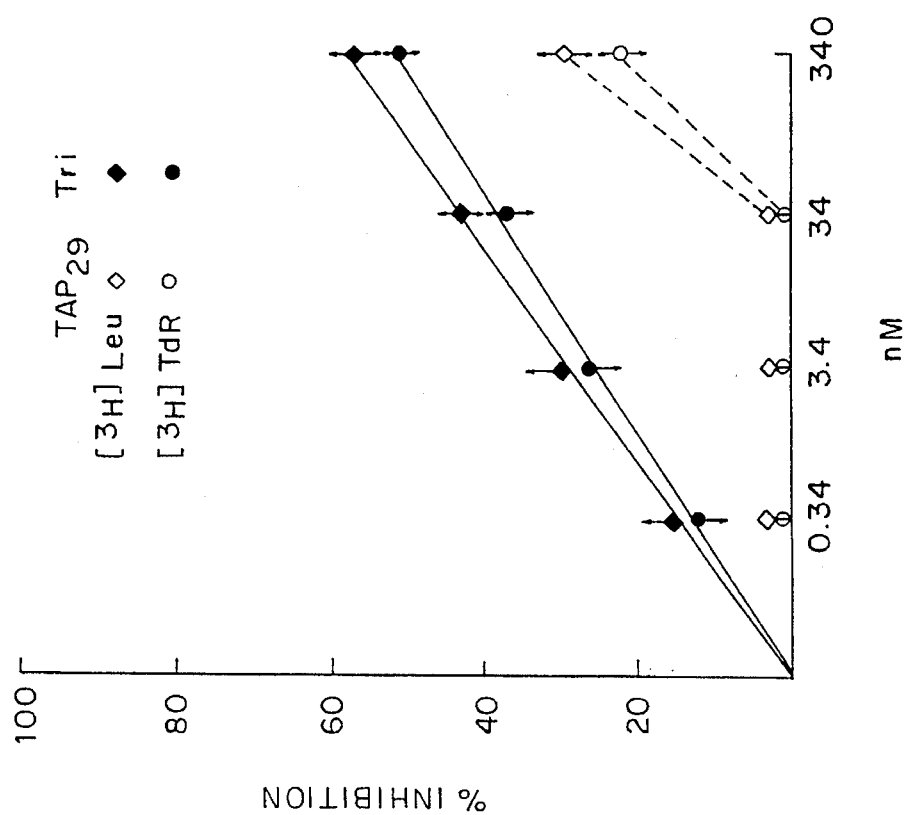
FIG. 5 is a graph comparing cytotoxicity of TAP 29 and trichosanthin. Cytotoxicity was measured by cellular incorporation of [$^3$H]thymidine (TdR) or [$^3$H]leucine (Leu) into TCA-precipitable products in pulse labeling experiments. H9 cells were seeded into 96-well plates at 2×$10^4$ cells/well. The culture was pulsed with 1 µCi (1Ci=37 GBq) of [$^3$H] thymidine or [$^3$H]leucine 8 hours prior to harvesting at 96 hours. Cellular DNA and protein synthesis were determined by scintillation counting of the incorporated labeled precursors. Results are normalized to values obtained for control cultures without drugs. Control cpm for labeled thymidine and leucine were 193×$10^3$ and 59×$10^3$ respectively. Results shown are averages of triplicates in two independent experiments. Standard deviations are indicated by error bars.
Figure 4:
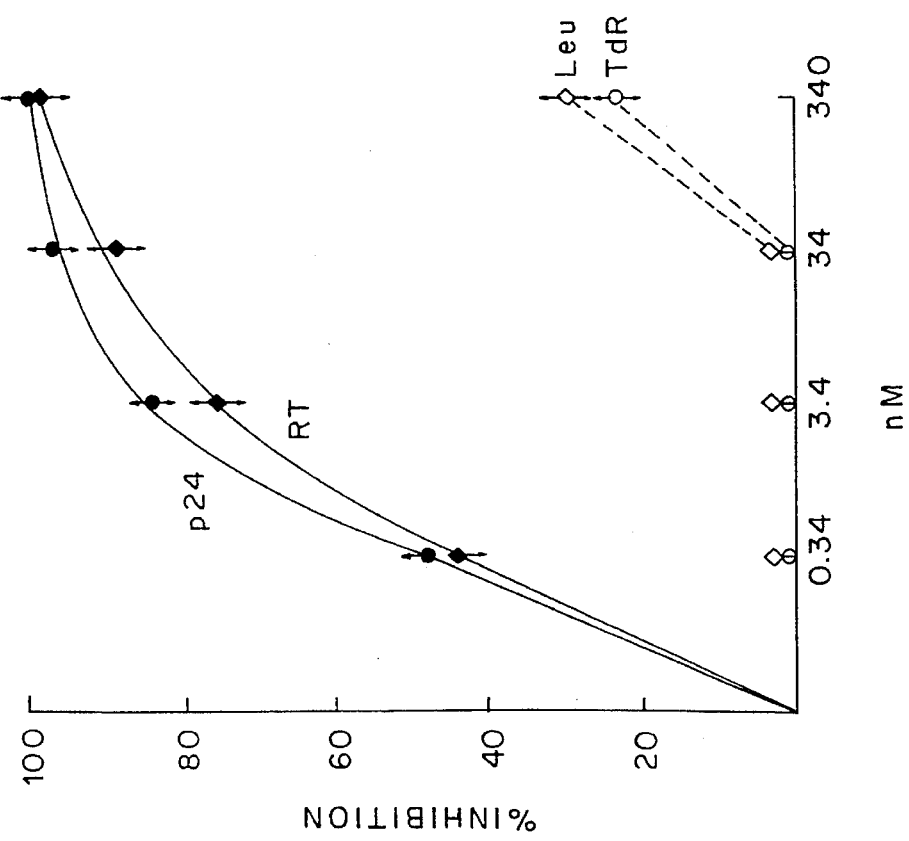
FIG. 4 is a graph showing the effect of TAP 29 on HIV infectivity as assessed by viral core antigen p24 expression and HIV-RT activity. p24 production was determined by RIA and expressed in ng/ml. Viral-RT activity was determined by the incorporation of [$^3$H]dTTP into TCA-precipitable products and expressed in terms of cpm ×$10^{-3}$/ml. These values in control culture (without the addition of TAP 29) were 2094 ng/ml and 796(×$10^{-3}$) cpm/ml, respectively, as determined in triplicate samples in two independent experiments. Results are normalized to values obtained in control cultures. Standard deviations are indicated by error bars.

The effect of TAP 29 on viral core protein p24 expression is shown in FIG. 4. TAP 29 exhibited dose-dependent inhibition of HIV-1 p24 expression. Inhibition of 47% and 97% was observed at 0.34 and 34 nM, respectively. An $ID_{50}$ of 0.37 nM was estimated from these results. The reduced production of p24 was not due to cytotoxic or cytostatic effects of the protein, and no decrease in cellular DNA or protein synthesis was observed at these concentrations of TAP 29. At 340 nM, or $1,000 \times ID_{50}$, less than 30% inhibition of cellular incorporation of [$^3$H] labeled thymidine or leucine was obtained. While a similar $ID_{50}$ was calculated for trichosanthin, as shown in FIG. 5, at the concentration used in assay, trichosanthin exhibited dose-dependent cytotoxicity to the host cells.

Inhibition of Viral Associated RT Activity.

The effects of TAP 29 on the activity of viral associated RT is also shown in FIG. 4. In this assay poly(rA).poly(dT)12–18 was used as template-primer and [$^3$H]dTTP as the substrate. The results are expressed as the polynucleotide incorporation of the [$^3$H]-labeled nucleotide in terms of cpm/ml. Here again, TAP 29 yielded dose-dependent inhibition of HIV-RT activity with an $ID_{50}$ of 0.46 nM. Trichosanthin, on other hand, exhibited a limited effective concentration range. Although a similar $ID_{50}$ was observed, significant cytotoxic effects were apparent.

EXAMPLE IV

TAP 29 HAS LOW TOXICITY TO INTACT CELLS

The cytotoxicity of the two anti-HIV proteins from Trichosanthes was compared by measuring their effects on cellular DNA and protein synthesis in uninfected H9 cells. The incorporation of [$^3$H]thymidine or [$^3$H]leucine into TCA precipitable DNA or protein was expressed as cpm/ml. A $10^3$ fold concentration range was tested and the results are summarized in FIG. 5. From 0.34 to 34 nM, TAP 29 caused no detectable effect on cellular incorporation of labeled thymidine or leucine, while p24 production and HIV-RT activity were inhibited more than 90%. At 340 nM, or $1,000 \times ID_{50}$, TAP 29 gave 22% and 30% reductions in cellular DNA and protein synthesis, respectively. Thus TAP 29 has a therapeutic index of at least 1,000. Trichosanthin, on the other hand, showed dose-dependent inhibition of cellular DNA and protein synthesis. At 3.4 nM ($10 \times ID_{50}$) trichosanthin caused about 26% and 31% inhibition of incorporation of [$^3$H]thymidine and [$^3$H]leucine, respectively. These results indicate that the therapeutic index of TAP 29 is at least two orders of magnitude higher than that of trichosanthin.

Inhibition of In Vitro Translation in Eukaryotic Cells

Figure 6:
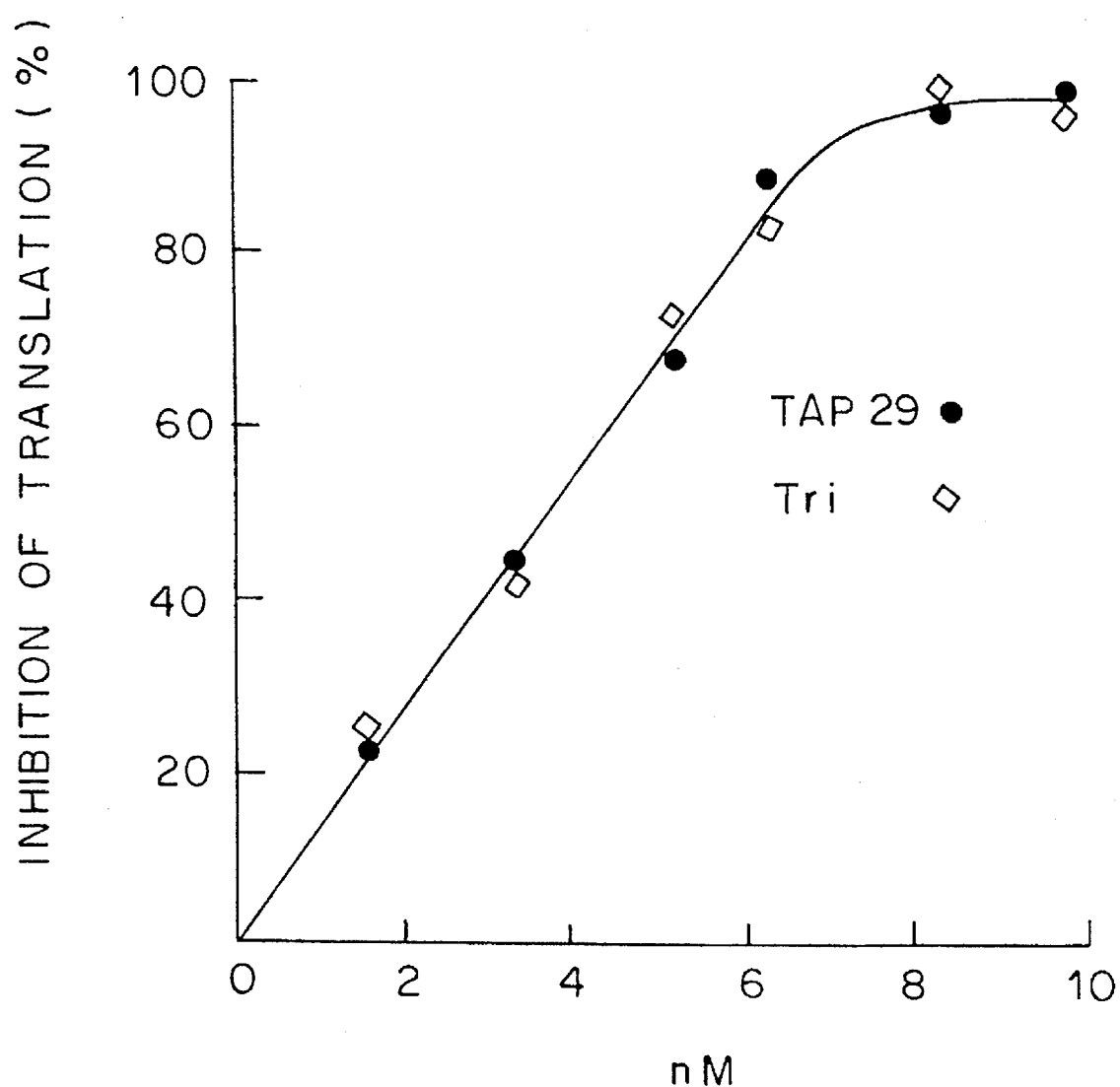
FIG. 6 is a graph showing the effect of TAP 29 on eukaryotic translation. Ribosome-inactivating activity of TAP 29 was measured by its effect on the in vitro translation of globin mRNA in a rabbit reticulocyte lysate system. Inhibition of protein biosynthesis was determined by the incorporation of [$^3$H]leucine into TCA-insoluble material as a function of TAP 29 concentration. Results were obtained from two independent experiments, each carried out in duplicate. Average control value (without the addition of TAP 29) was 5.9×$10^4$ cpm/µl. Errors are within 4% of the mean.

Both TAP 29 and trichosanthin possess ribosome-inactivating activity, measured by reduction of in vitro translation in a rabbit reticulocyte lysate system (Pelham, R. B. et al., Eur. J. Biochem. 67:247–256 (1976)). The results are shown in FIG. 6. Both proteins exhibited a dose-dependent inhibition of cell-free translation with a similar $ID_{50}$ of about 3.7 nM.

Like ricin and trichosanthin, TAP 29 also inhibits in vitro translation of eukaryotic cells. Distinct from these compounds, TAP 29 is not toxic to intact normal cells.

Ricin is a plant toxin, composed of two 25 kDa subunits (A and B chains) linked by a disulfide bridge. The B chain of the toxin binds to the surface of eukaryotic cells and enables the entrance of the A chain. The A chain is the catalytic subunit of the molecule, which upon internalization inhibits protein synthesis in the cell. TAP 29 is clearly different from ricin in that it is a single chain polypeptide, and it is not toxic to intact cells.

Trichosanthin is a 26 kDa plant protein isolated from the root tuber of Trichosanthes which can inhibit protein synthesis in vitro (Maraganore, J. M. et al., J. Biol. Chem. 262:11628–11633 (1987)). It is important to note that under identical assay conditions, TAP 29 is much less cytotoxic as compared to trichosanthin (see Table 2). The low in vitro cytotoxicity of TAP 29 indicates that it may have a much better therapeutic index.

EXAMPLE V

MOLECULAR CLONING OF TAP 29

Poly A+ mRNA is prepared from Trichosanthes kirilowii as described above. Genomic and cDNA libraries are constructed in lambda gt11 as described above. The library is screened by plaque hybridization using oligonucleotide probes derived from the N-terminal amino acid sequence of TAP 29.

Clones are obtained and sequenced according to standard methods (see above) to determine the nucleotide sequence of the TAP 29 gene, and, from this, the amino acid sequence of the entire TAP 29 protein. The cloned gene is expressed in bacterial and eukaryotic cells according to methods described above.

EXAMPLE VI

CONJUGATION OF TAP 29 TO ANTI-HIV ANTIBODIES

TAP 29 is cross-linked to human anti-gp41 and human anti-gp120 monoclonal antibodies using the heterobifunctional reagent, SPDP (N-succinimidyl 3-(2-pyridyldithio-)propionate. Purified antibody in phosphate buffered saline is treated with SPDP in 10–15-fold molar excess for 30 min. at room temperature so as to introduce 2-pyridyl disulfide groups into the IgG molecule. The free SPDP is removed by dialysis. The sample is then mixed with TAP 29 (3-fold molar excess) at 4° C. for 16 hours. The conjugate is separated from unbound TAP 29 by gel filtration on a Sephacryl S-200 column.

The cytotoxic effect of the conjugate is tested on CEM-ss and H9 cells, as described above. The conjugate is shown to have specific cytotoxic activity for HIV infected, but not for uninfected target cells.

The conjugate is used to treat a subject with and HIV infection or AIDS by administration as described above.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

| Asp | Val | Ser | Phe | Arg | Leu | Ser | Gly | Ala | Thr | Ser | Lys | Lys | Lys | Val | Tyr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Phe | Ile | Ser | Asn | Leu | Arg | Lys | Ala | Leu | Pro | Asn | Glu | Lys | Lys | Leu | Tyr |
|     |     |     | 20  |     |     |     |     | 25  |     |     |     | 30  |     |     |     |
| Asp | Ile | Pro | Leu | Val | Arg | Ser | Ser | Xaa | Ser | Gly | Ser | Lys |
|     |     | 35  |     |     |     |     | 40  |     |     |     |     | 45  |

( 2 ) INFORMATION FOR SEQ ID NO:2:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

| Asp | Val | Ser | Phe | Arg | Leu | Ser | Gly | Ala | Thr | Ser | Ser | Ser | Tyr | Gly | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Phe | Ile | Ser | Asn | Leu | Arg | Lys | Ala | Leu | Pro | Asn | Glu | Arg | Lys | Leu | Tyr |
|     |     |     | 20  |     |     |     |     | 25  |     |     |     | 30  |     |     |     |
| Asp | Ile | Pro | Leu | Ile | Arg | Ser | Ser | Leu | Pro | Gly | Ser |
|     |     | 35  |     |     |     |     | 40  |     |     |     |     |

( 2 ) INFORMATION FOR SEQ ID NO:3:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:3:

AAR AAR AAR GTN TA                                                                              14

What is claimed is:

1. An isolated TAP 29 protein, obtainable from the root tuber of a plant of the genus Trichosanthes, wherein said protein; (a) includes the amino acid sequence SEQ ID NO:1; (b) has anti-HIV activity in vitro at concentrations above about 0.3 nanomolar; (c) lacks non-specific cytotoxicity in vitro at concentrations of about 1.5 to 30 nanomolar; and (d) has a molecular weight of about 29 kDa as determined by sodium dodecyl sulfate-polyacrylamide electrophoresis.

* * * * *